United States Patent
Piech et al.

(10) Patent No.: US 9,322,803 B2
(45) Date of Patent: Apr. 26, 2016

(54) DETECTOR HAVING A SINGLE SOURCE FOR IONIZATION AND PHOTO DETECTION

(75) Inventors: Marcin Piech, East Hampton, CT (US); Sameh Dardona, South Windsor, CT (US); Joseph V. Mantese, Ellington, CT (US); Michael T. Gorski, Clinton, CT (US)

(73) Assignee: UTC FIRE & SECURITY CORPORATION, Farmington, CT (US)

( * ) Notice: Subject to any disclaimer, the term of this patent is extended or adjusted under 35 U.S.C. 154(b) by 175 days.

(21) Appl. No.: 13/980,117

(22) PCT Filed: Jan. 22, 2011

(86) PCT No.: PCT/US2011/000110
§ 371 (c)(1),
(2), (4) Date: Jul. 17, 2013

(87) PCT Pub. No.: WO2012/099564
PCT Pub. Date: Jul. 26, 2012

(65) Prior Publication Data
US 2013/0293870 A1    Nov. 7, 2013

(51) Int. Cl.
G01N 27/64 (2006.01)
G01N 21/53 (2006.01)
G08B 17/10 (2006.01)
G01N 27/66 (2006.01)

(52) U.S. Cl.
CPC .............. *G01N 27/64* (2013.01); *G01N 21/53* (2013.01); *G08B 17/10* (2013.01); *G01N 27/66* (2013.01)

(58) Field of Classification Search
CPC ....... G01N 27/64; G01N 27/66; G01N 21/53; G01N 21/67; G01N 21/69; G01N 21/27; G01N 21/278; G08B 17/107; G08B 17/10; G01J 3/443
See application file for complete search history.

(56) References Cited

U.S. PATENT DOCUMENTS

| 4,469,953 | A |   | 9/1984  | Fujisawa et al. |            |
|-----------|---|---|---------|-----------------|------------|
| 5,572,137 | A | * | 11/1996 | Jones           | G01N 27/66 |
|           |   |   |         |                 | 250/382    |
| 5,633,501 | A |   | 5/1997  | Amleshi et al.  |            |
| 6,012,326 | A | * | 1/2000  | Raybone         | G01N 21/73 |
|           |   |   |         |                 | 422/186.21 |

(Continued)

FOREIGN PATENT DOCUMENTS

| CN | 201322713 Y | 10/2009 |
|----|-------------|---------|
| JP | 5229288 A | 7/2013 |
| WO | WO 2008007084 A1 * | 1/2008 |

OTHER PUBLICATIONS

Chinese Search Report for CN Application No. 201180065634.X, dated Sep. 19, 2014.

(Continued)

*Primary Examiner* — Kara E Geisel
*Assistant Examiner* — Violeta A Prieto
(74) *Attorney, Agent, or Firm* — Carlson, Gaskey & Olds

(57) ABSTRACT

An exemplary detector includes a source of radiation. A detection chamber is configured to at least temporarily contain a fluid. At least some of the radiation ionizes at least some of the fluid. At least some of the radiation produces light in the detection chamber. An ionization sensor provides an output corresponding to an amount of fluid ionization in the detection chamber. A light sensor provides an output corresponding to an amount of the light detected by the light sensor.

20 Claims, 4 Drawing Sheets

(56) References Cited

U.S. PATENT DOCUMENTS

| | | | |
|---|---|---|---|
| 6,057,774 | A | 5/2000 | Venzant |
| 6,195,014 | B1 | 2/2001 | Sakurai et al. |
| 6,351,219 | B1 | 2/2002 | Tanguay et al. |
| 6,362,743 | B1 * | 3/2002 | Tanguay et al. ............... 340/630 |
| 6,737,977 | B2 | 5/2004 | Nishikawa et al. |
| 6,756,905 | B2 | 6/2004 | Rattman et al. |
| 2007/0285265 | A1 * | 12/2007 | Lax ............................... 340/632 |
| 2008/0061763 | A1 * | 3/2008 | Nutting .................... G01V 3/14 324/71.1 |
| 2009/0128821 | A1 * | 5/2009 | Sugimoto ............ G01N 21/274 356/438 |
| 2009/0303484 | A1 * | 12/2009 | Hofeldt .................. B65H 20/00 356/431 |
| 2010/0032560 | A1 * | 2/2010 | Allsworth ..................... 250/282 |
| 2012/0170718 | A1 * | 7/2012 | Travish et al. ................ 378/122 |

OTHER PUBLICATIONS

International Search Report and Written Opinion of the International Searching Authority for International application No. PCT/US2011/000110 dated Oct. 28, 2011.

* cited by examiner

DETECTOR HAVING A SINGLE SOURCE FOR IONIZATION AND PHOTO DETECTION

BACKGROUND

Various detectors are known. Some are configured for smoke detection. Others are useful for detecting toxic gases, for example. Many such detectors use ionization for detecting the presence or amount of the substance or gas of interest.

One known type of smoke detector includes Americium 241 as a source of alpha particles used for ionizing air. Alpha particles admitted from the Americium 241 pass into the smoke detector internal space where they ionize the air within that space. When smoke enters into the internal space, the smoke interacts with the ions and alters the ion concentration and distribution within the internal space. This can be detected, for example, by measuring the voltage or current at a collector electrode of the smoke detector.

Another known type of smoke detector utilizes light for detecting smoke particles. A light source emits light into the smoke detector internal space. A photo-sensitive detector is positioned to receive some or none of the light emitted from the light source. When smoke enters into the internal space, the smoke absorbs and scatters light from the light source. This can be detected, for example, by measuring scattered light intensity or a change in light intensity.

There have been attempts to combine ionization and photoelectric smoke detectors to provide both technologies in a single housing. For example, U.S. Pat. No. 5,633,501 describes a smoke detector that uses a source of light for photoelectric smoke detection and a source of ions for ionizing smoke detection within the same unit.

SUMMARY

An exemplary detector includes a source of radiation. A detection chamber is configured to at least temporarily contain a fluid. At least some of the radiation ionizes at least some of the fluid. At least some of the radiation produces light in the detection chamber. An ionization sensor provides an output corresponding to an amount of fluid ionization in the detection chamber. A light sensor provides an output corresponding to an amount of the light detected by the light sensor.

One example detector is configured for smoke detection. The fluid within the detection chamber is ambient air. Smoke in the detection chamber results in an output from the ionization sensor, the light sensor or both that is indicative of the presence of smoke. Such an example only requires a single source to detect smoke using ionization and photo-electric capabilities.

The various features and advantages of disclosed examples will become apparent to those skilled in the art from the following detailed description. The drawings that accompany the detailed description can be briefly described as follows.

DETAILED DESCRIPTION

Figure 1:
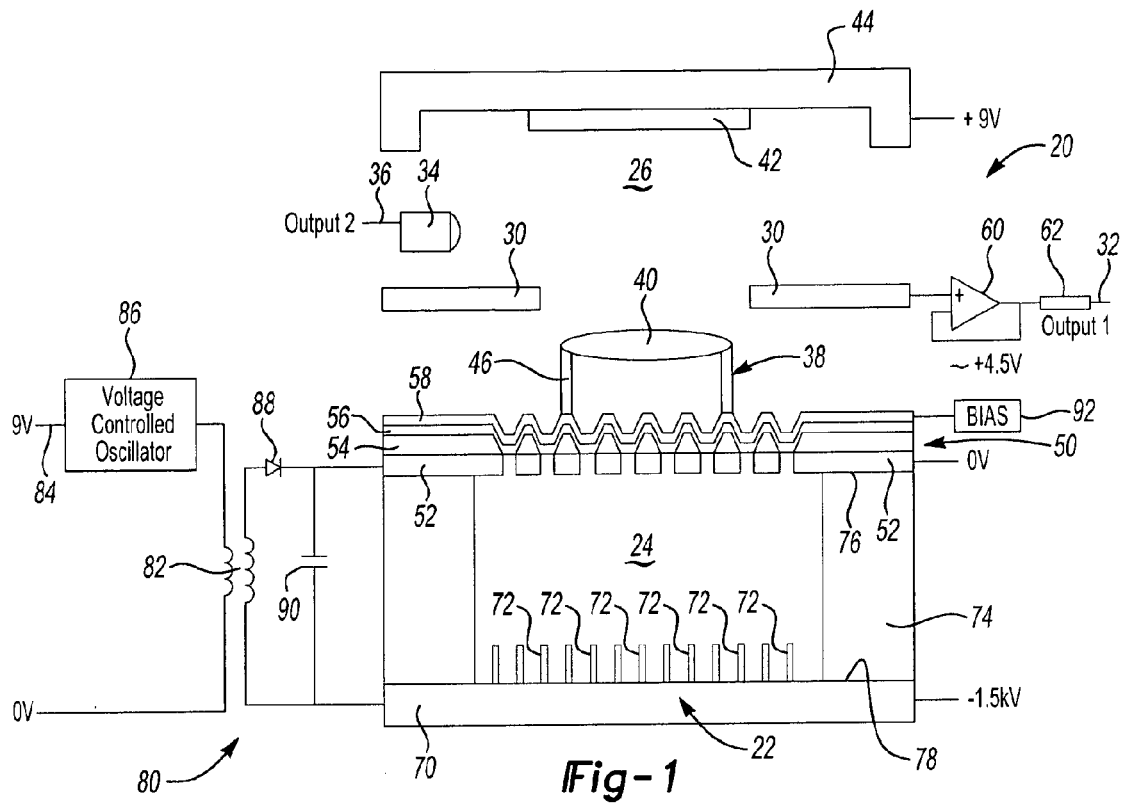
FIG. 1 schematically illustrates an example detector arrangement designed according to an embodiment of this invention.

FIG. 1 schematically shows an example detector 20 that can be used for detecting a substance of interest. For purposes of discussion, the detector 20 will be described as a smoke detector. Detectors designed according to an embodiment of this invention are not necessarily limited to smoke detectors.

The example detector 20 includes a source of radiation 22, a pressurized chamber 24 and a detection chamber 26. In this example, the detection chamber 26 is configured to allow ambient air to pass through the detection chamber 26. Smoke (or another substance or gas of interest) can also enter the detection chamber 26 whenever it is present in the vicinity of the detector 20. An ionization sensor 30 provides an output at 32 corresponding to an amount of ionization in the detection chamber 26. The output at 32 is configured to indicate when smoke is in the detection chamber 26 so that an appropriate alarm can be provided. A light sensor 34 provides an output at 36 corresponding to an amount of light detected by the light sensor 34. The output at 36 is configured to indicate when smoke is in the detection chamber 26 so that an appropriate alarm can be provided. In some situations only one of the outputs 32 or 36 will indicate the presence of smoke while in others both outputs indicate that smoke is present.

The single source of radiation 22 facilitates ionization-type detection and photo detection within the detection chamber 26. Some of the radiation from the source 22 passes through the pressurized chamber 24 and into the detection chamber 26 for purposes of ionizing fluid (e.g., air) in the detection chamber 26. Some of the radiation from the source 22 passes through the pressurized chamber 24 and into a light chamber 38 for generating light that is used for photo detection within the detection chamber 26.

Depending on the fluid or substances within the detection chamber 26, some of that light may be detected by the light sensor 34. This example includes directing or aiming light from the light chamber 38 through a window or lens 40 toward a light absorbing element 42, which is supported on a structure 44 that defines part of the perimeter of the detection chamber 26. In one example, if only air is present in the detection chamber 26, the light will be absorbed by the light absorbing element 42 and not detected by the light sensor 34. If smoke is present within the detection chamber 26, on the other hand, smoke particles will defract or scatter at least some of the light such that it is detectable by the light sensor 34.

In this example, the light chamber 38 includes the window or lens 40 and a sidewall 46. Another side of the light chamber 38 is defined by a window 50. The sidewall 46 is received against the window in a sealed manner so that the light chamber 38 is a closed chamber in this example.

The light chamber 38 is filled with an inert gas, for example. Example gases for this purpose include nitrogen, neon, argon, krypton or xenon. In one example, the light chamber is maintained at a pressure between about 1 torr and 760 torr. Electrons (i.e., radiation from the source 22) passing through the window 50 interact with the inert gas within the light chamber 38 resulting in generated light. Such light passes through the window or lens 40 into the detection chamber 26 in the direction of the light absorbing element 42. The light emitted from the light chamber 38 has a wavelength and a range from about 180 nm to about 3,000 nm.

The illustrated window 50 includes an extraction grid 52 comprising an electrically conductive material. A supporting grid 54 is between the extraction grid 52 and a membrane 56 that is permeable to electrons so that it allows a sufficient amount of electrons to pass through to accomplish the desired ionization and light generation in the detection chamber 26. A conductive film 58 is provided over the membrane 56 in this example.

In some examples, the extraction grid 52 is bonded to the supporting grid 54. In other examples, a single layer includes the extraction grid 52 and the supporting grid 54. In the illustrated example, the membrane 56 is deposited onto the supporting grid 54, for example, by chemical vapor deposition. The conductive film 58 is deposited onto the membrane 56, for example, by chemical vapor deposition or a sputtering process. In some examples, the membrane 56 and the conductive film 58 comprise a single layer rather than distinct layers as shown in the illustration. In this example, the sidewall 46 of the light chamber 38 is received against the conductive film 58.

The source of radiation 22, therefore, operates as a source of radiation for generating light useful for photo detection of smoke (or another substance of interest) within the detection chamber 26. The source of radiation 22 also operates as a source of radiation for ionization of a fluid within the detection chamber 26.

The ionization sensor 30 in this example comprises a collector electrode positioned within the detection chamber 26. The collector electrode 30 is connected to an amplifier 60 and resistor 62 for conditioning the signal from the collector electrode to provide a suitable output at 32. The example detector 20 uses ionization detection techniques for detecting smoke within the detection chamber 26 according to known principles of such ionization detection.

The illustrated example sensor 20 is unique in that it includes a single source of radiation 22 that is useful for ionization and photo detection. One feature of having a single source is that it provides a more economical arrangement because multiple sources are not required, which reduces cost, component and size requirements for a sensor.

In the example of FIG. 1, the single source of radiation 22 includes an electrically conductive substrate 70 and a plurality of nanometer scale elongate structures 72 for generating electrons. In one example, the structures 72 operate as field-emission, cold-cathode nanoemitters. Electrons from the source 22 pass through the pressurized chamber 24. A sufficient amount of electrons pass through window 50 in some examples to accomplish the desired detection in the detection chamber 26.

In one example, the pressurized chamber 24 is maintained at a vacuum pressure. One example includes a pressure on the order of $10^{-3}$ torr. A spacer 74 establishes a distance between the elongate structures 72 and the window 50. The spacer 74 is made from an electrically non-conductive material having one end 76 secured to the window 50 and an opposite end 78 secured to the substrate 70.

The example of FIG. 1 includes voltage converter circuitry 80 including a transformer 82 that converts an input voltage from a voltage source 84 into an output voltage in the range from about 0.5 kV to 5 kV. In one example, the output voltage is approximately 1.6 kV.

A voltage controlled oscillator 86 converts the input voltage from the voltage source 84 (e.g., a 9 volt battery) to a 9 volt AC current that is input to the transformer 82. A first output line of the transformer 82 is connected to the extraction grid 52 through a diode 88 that rectifies the output from the transformer 82. A reservoir capacitor 90 is connected between the output lines of the transformer 82 and smoothes the output voltage. In the illustrated example, the extraction grid 52 is maintained at 0 volts. The voltage converting circuit 80 applies a voltage in the range from about −0.5 kV to −5 kV to the substrate 70 in comparison to the 0 volts of the extraction grid 52. In one example, −1.5 kV is applied to the substrate 22.

The conductive film 58 is exposed to the space within the detection chamber 26 and the light chamber 38 at respective locations on the conductive film 58. An electrical bias 92 is applied to the conductive film 58 within a range from about −0.5 kV to about 0.5 kV. The bias 92 may be controlled to alter the operating characteristics of the detector 20 such as increasing or decreasing the sensitivity as needed. In one example, the bias 92 includes voltage converter circuitry similar to that shown at 80 and obtains the bias potential from the same voltage source 84 that is used to power the voltage converting circuitry 80.

Figure 2:
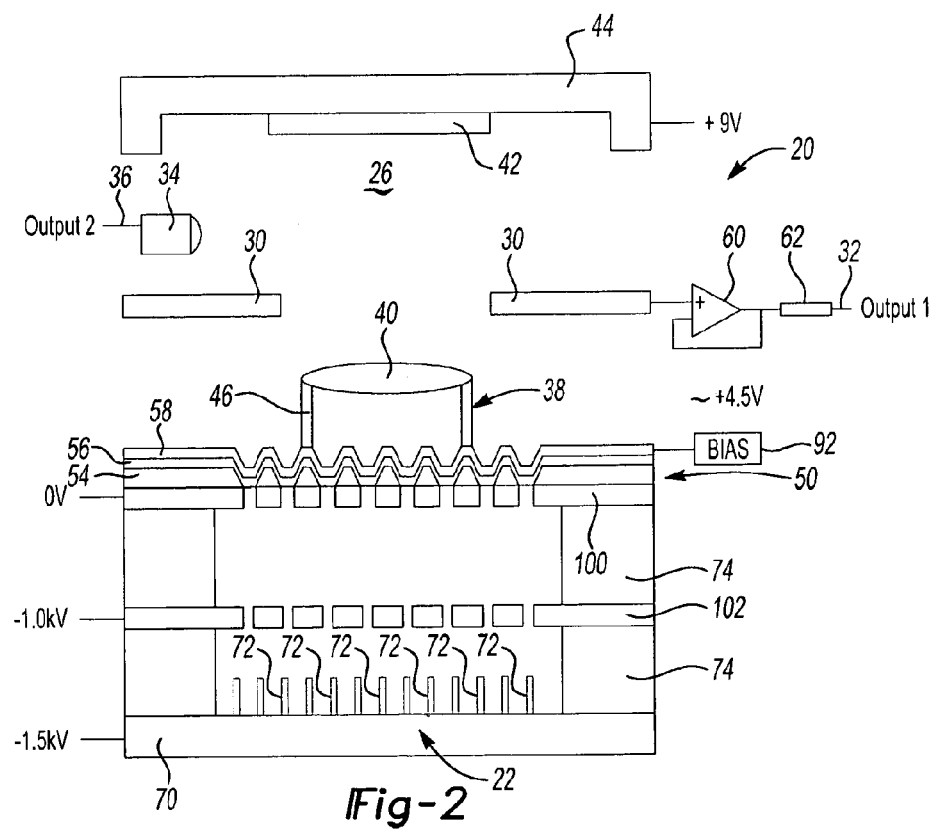
FIG. 2 illustrates another example detector.

FIG. 2 illustrates another example sensor 20. This example includes a triode-type single source of radiation arrangement based on field-emission from cold-cathode nanoemitters. In this example, the window 50 includes the conductive film 58, the transparent membrane 56 and the supporting grid 54 like those in the example of FIG. 1. In this example, an acceleration grid 100 made of an electrically conductive material is bonded to the spacer 74. The supporting grid 54 is bonded to the acceleration grid 100. An extraction grid 102 is positioned closer to the nano-sized elongate structures 72 to generate a high field in the vicinity of those structures. The extraction grid 102 facilitates extracting electrons using a known cold-cathode field-emission process. In some examples, the extraction grid 102 is maintained at a potential of about 0.2 to 1.5 kV higher than that of the substrate 70. One example includes a potential difference between the extraction grid 102 and that of the substrate 70 that is approximately 0.5 kV.

The extraction grid 102 serves the purpose of accelerating electrons generated in the vicinity of the nano-sized elongate structures 72 toward the window 50. Electrons that pass through the extraction grid 102 are further accelerated by the potential difference between the extraction grid 102 and the acceleration grid 100.

Figure 3:
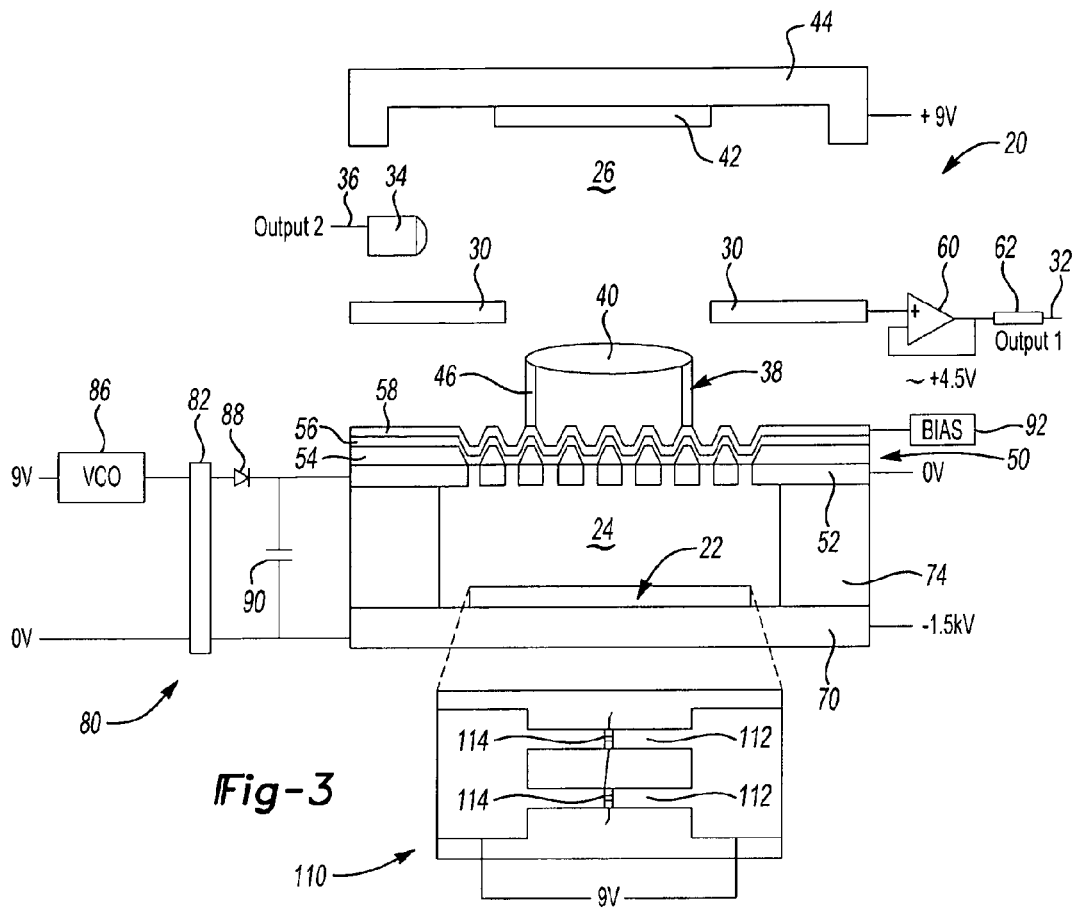
FIG. 3 schematically illustrates another example detector.

FIG. 3 illustrates another example detector arrangement including another type of single source of radiation 22 to achieve the dual functionality of the sensor based upon ionization-type detection and photo detection. In this example, the source 22 includes an array 110 of electron emitting elements 112. A small fissure 114 in the electron emitting elements 112 has a width of less than 10 micrometers. Upon application of an electric field to the electron emitting elements 112, electrons are emitted into the pressurized (e.g., evacuated) chamber 24. At least some of those electrons pass through the window structure 50 to accomplish the desired detection in the detection chamber 26.

Figure 4:
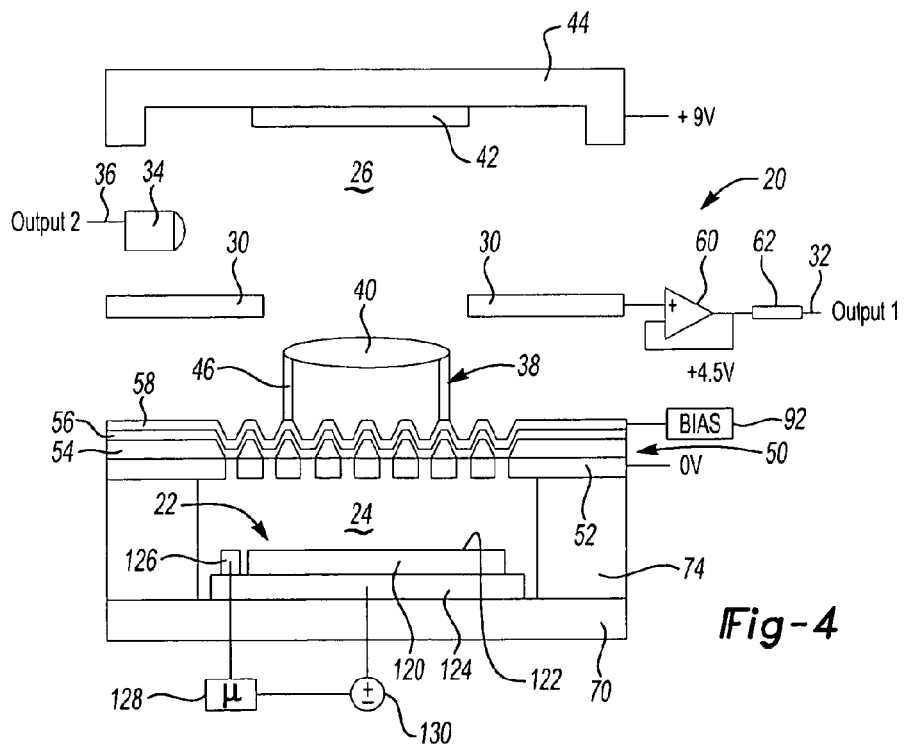
FIG. 4 schematically illustrates another example detector.

FIG. 4 illustrates another example including a pyroelectric electronic accelerator as the source 22. This example includes a pyroelectric crystal 120 with a crystallographic Z surface 122 exposed to the chamber 24 and facing the window 50. A change in the polarization of the Z surface 122 causes electron acceleration away from that surface and toward the window 50. This is a known phenomenon that occurs when the temperature of a pyroelectric crystal changes in a dilute gas environment, for example. When the crystal surface is negatively charged in a vacuum or reduced pressure environment, electrons in close proximity become accelerated away from the Z surface.

The example pyroelectric electronic accelerator source of radiation 22 includes a temperature control element 124, a temperature sensor 126, a controller 128 and a voltage source 130. A desired amount of electron acceleration is achieved by controlling the temperature of the pyroelectric crystal 120 of the accelerator. The temperature control element 124 associated with the accelerator establishes a temperature that facilitates electron acceleration toward the window 50. The temperature sensor 126 provides temperature information to the microcontroller 128. Desired operation of the temperature control element 124 is achieved by the controller 128 controlling the voltage source 130 so that a desired amount of electron acceleration is realized.

In one example, the temperature control element 124 comprises a heater. The chamber 24 in one such example is filled with gas such as air, helium, nitrogen, argon, hydrogen, oxygen or a mixture of these. The chamber 24 in one such example is maintained at a pressure of less than about $10^{-3}$ torr.

One difference between the example embodiment of FIG. 4 and those of FIGS. 1-3 is that no voltage converter circuit is needed for generating high potential for accelerating electrons from the radiation source 22.

Figure 5:
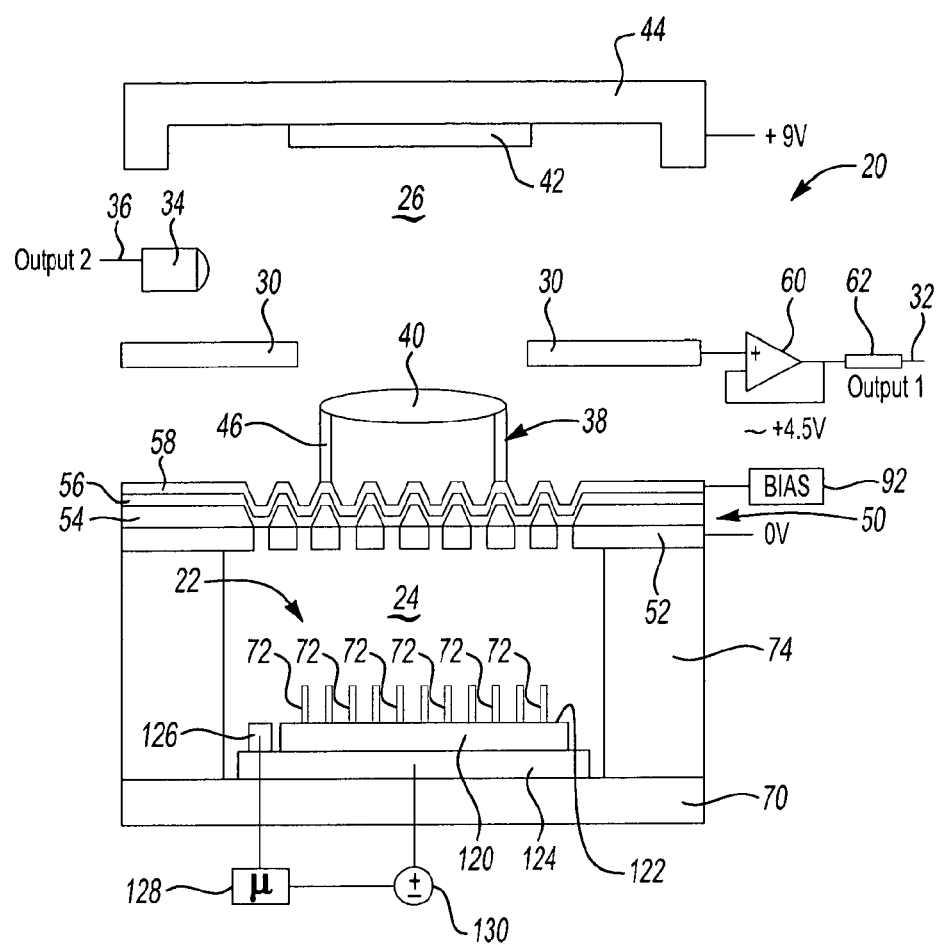
FIG. 5 schematically illustrates another example detector.

FIG. 5 shows another example sensor configuration that operates based on creating high electric fields near cold-cathode nanoemitters by inducing large polarization changes of a pyroelectric crystal surface attached to the nanoemitters. In this example the source 22 includes elongate nano-sized structures 72 that are attached to the pyroelectric crystal 120. The crystallographic Z surface 122 is still exposed to the chamber 24 facing the window 50.

In this example, when the polarization of the Z surface 122 changes, this generates a high electric field near the tips of the elongate nano-sized structures 72. This results in electron emission and acceleration away from these nano-sized structures 72 toward the window 50. Like the example of FIG. 4, a desired amount of electron acceleration is achieved by controlling the temperature of the pyroelectric crystal 120. The temperature sensor 126, microcontroller 128 and voltage source 130 are used for this purpose in the same manner as described above with regard to FIG. 4.

Figure 6A:
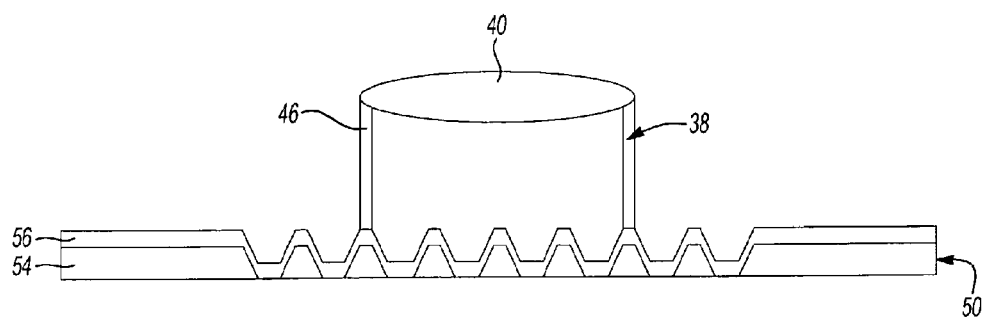
FIGS. 6A-6C schematically illustrate respective configurations of a window that is useful in detectors designed according to embodiments of this invention.

FIG. 6A shows an alternative configuration of the window 50. In this example, there is no conductive film used on top of the membrane 56 that is permeable to electrons. The membrane 56 is bonded to the supporting grid 54 in the illustrated example.

Figure 6B:
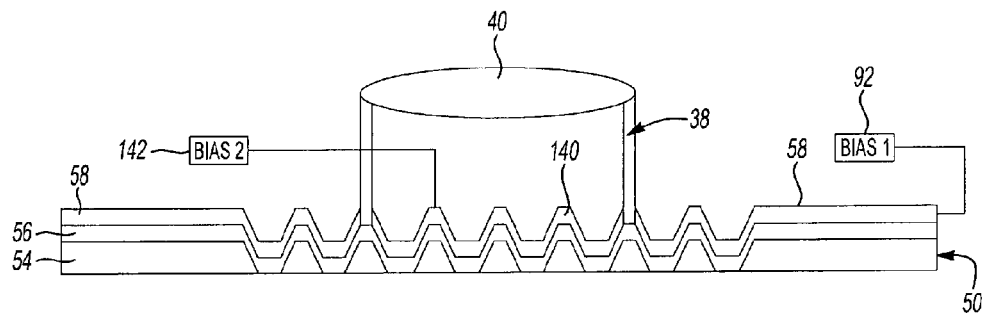

The example of FIG. 6B includes a window 50 that includes the supporting grid 54 and the membrane 56. The conductive film 58 is placed on the portions of the membrane 56 that are exposed to the space within the detection chamber 26 but not placed on the portions that are within the light chamber 38. In this example, a second conductive film 140 is placed over the membrane 56 within the light chamber 38. The conductive films 58 and 140 are electrically isolated from each other.

This example includes applying a second bias 142 to the conductive film 140 within the light chamber 38. Having two biases 92 and 142 allows for separate and different electrical potentials to be placed on each of the conductive films. Utilizing two different biases for the different films provides enhanced control over the two detecting mechanisms of the detector. The bias 92 can be tuned to achieve enhanced ionization-based detection functionality within the detection chamber. Similarly, the bias 142 can be tuned to enhance operation of the light-based detection functionality of the detector.

One alternative includes eliminating the conductive film 140. Another example includes eliminating the conductive film 58. The example of FIG. 6A shows an arrangement in which both such films have been eliminated compared to the example of FIG. 6B.

In additional embodiments of the foregoing examples, the radiation may include the generation of x-rays, and where sufficient x-rays are generated and utilized to generate ionization within the detection chamber 26, or to generate light within the light chamber 38 or both, to achieve the desired detection characteristics of the detector. The generation of x-rays may for example occur as a result of deceleration of the electrons when passing through the chamber space 24, or through the window 50, or both.

Figure 6C:
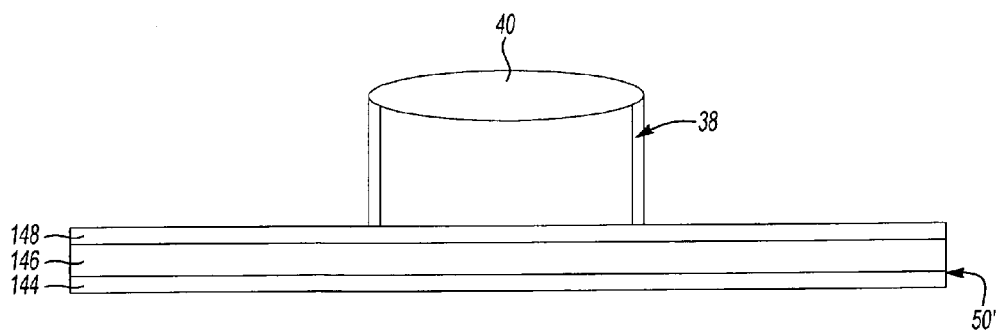

The example of FIG. 6C includes a window 50' having a conductive metal layer 144, a supporting membrane 146 and a conductive film 148. The window 50' in this example is not permeable to electrons. Instead the window 50' is a target that produces x-rays responsive to electrons hitting the target. The window 50' in one example becomes a source of soft x-rays utilized for ionization within the detection chamber 26 and for generating light within the light chamber 38. Soft x-ray generation occurs in a known manner in one example.

In one example, the conductive metal layer 144 comprises an aluminum foil having a thickness in the range from about 80 nanometers to about 240 nanometers. The conductive film 148 provides control over the ionization process within the detection chamber and the generation of light within the light chamber 38. It is possible to partition the conductive film 148 in a manner similar to that used in the example of FIG. 6B to allow more customized control over the ionization process within the detection chamber 26 for ionization detection and over the generation of light within the light chamber 38 for photo detection, respectively.

While various examples are shown with differing features, it is possible to combine one or more features from one disclosed example with another of the disclosed examples to realize another combination of features even though such a combination is not necessarily specifically illustrated in the drawings or described above.

The preceding description is exemplary rather than limiting in nature. Variations and modifications to the disclosed examples may become apparent to those skilled in the art that do not necessarily depart from the essence of this invention. The scope of legal protection given to this invention can only be determined by studying the following claims.

We claim:
1. A detector, comprising:
 a single source of radiation, wherein the single source comprises at least one of
  a diode-based field-emission electron source,
  a triode-based field-emission electron source,
  a gap-based field-emission electron source,
  a pyroelectric crystal-based accelerator electron source, and
  a combined pyroelectric crystal and nanoemitter based accelerator electron source;
 a detection chamber configured to at least temporarily contain a fluid, at least some of the radiation from the single source of radiation ionizing at least some of the fluid, at least some of the radiation from the single source of radiation producing light in the detection chamber;
 an ionization sensor that provides an output corresponding to an amount of fluid ionization in the detection chamber; and
 a light sensor that provides an output corresponding to an amount of the light detected by the light sensor.

2. The detector of claim 1, comprising
 a light chamber containing molecules that generate light responsive to at least some of the radiation entering the light chamber, the light chamber is situated such that the generated light enters the detection chamber.

3. The detector of claim 2, wherein the light chamber includes at least one light-permeable surface facing toward the detection chamber.

4. The detector of claim 3, wherein the light-permeable surface comprises a lens.

5. The detector of claim 2, wherein the molecules are inert gas molecules.

6. The detector of claim 5, wherein the inert gas comprises at least one of nitrogen, neon, argon, krypton and xenon.

7. The detector of claim 2, wherein the light chamber is within the detection chamber.

8. The detector of claim 2, comprising
a pressurized chamber adjacent the detection chamber, the source of radiation being at least partially in the pressurized chamber, the pressurized chamber having a window through which at least some of the radiation passes from the pressurized chamber to the detection chamber; and
wherein the light chamber is adjacent the pressurized chamber such that at least some of the radiation passing through the window enters the light chamber.

9. The detector of claim 8, wherein the pressurized chamber window defines one side of the light chamber.

10. The detector of claim 1, comprising a controller that communicates with the ionization sensor and the light sensor, the controller providing an indication when the output from at least one of the ionization sensor or the light sensor indicates a selected condition.

11. The detector of claim 1, wherein the fluid comprises a gas and the ionization sensor or the light sensor provides an output that indicates whether a gas of interest is in the detection chamber.

12. The detector of claim 1, wherein the fluid comprises air and the ionization sensor or the light sensor provides an output that indicates whether smoke is in the detection chamber.

13. The detector of claim 1, wherein the ionization sensor detects an ionization current of the fluid in the detection chamber.

14. The detector of claim 1, wherein the light sensor comprises a photo-detector.

15. The detector of claim 1, wherein the light sensor is positioned outside of a direct path of light entering the detection chamber such that the light sensor detects light that is deflected by particles of interest in the detection chamber.

16. The detector of claim 1, wherein the light in the detection chamber has a wavelength in a range from about 180 nm to about 3000 nm.

17. The detector of claim 1, wherein the radiation includes x-rays.

18. A detector, comprising:
a single source of radiation, wherein the radiation includes x-rays;
a detection chamber configured to at least temporarily contain a fluid, at least some of the radiation from the single source of radiation ionizing at least some of the fluid, at least some of the radiation from the single source of radiation producing light in the detection chamber;
an ionization sensor that provides an output corresponding to an amount of fluid ionization in the detection chamber; and
a light sensor that provides an output corresponding to an amount of the light detected by the light sensor.

19. A detector, comprising:
a single source of radiation, wherein the single source comprises at least one of
a diode-based field-emission electron source,
a triode-based field-emission electron source, and
a gap-based field-emission electron source;
a detection chamber configured to at least temporarily contain a fluid, at least some of the radiation from the single source of radiation ionizing at least some of the fluid, at least some of the radiation from the single source of radiation producing light in the detection chamber;
an ionization sensor that provides an output corresponding to an amount of fluid ionization in the detection chamber; and
a light sensor that provides an output corresponding to an amount of the light detected by the light sensor.

20. A detector, comprising:
a single source of radiation, wherein the single source comprises at least one of
a pyroelectric crystal-based accelerator electron source, and
a combined pyroelectric crystal and nano emitter based accelerator electron source;
a detection chamber configured to at least temporarily contain a fluid, at least some of the radiation from the single source of radiation ionizing at least some of the fluid, at least some of the radiation from the single source of radiation producing light in the detection chamber;
an ionization sensor that provides an output corresponding to an amount of fluid ionization in the detection chamber; and
a light sensor that provides an output corresponding to an amount of the light detected by the light sensor.

* * * * *